United States Patent
Kawanishi

(10) Patent No.: US 7,634,312 B2
(45) Date of Patent: *Dec. 15, 2009

(54) VISCERAL FAT DETERMINING DEVICE

(75) Inventor: Shozo Kawanishi, Akashi (JP)

(73) Assignee: Yamato Scale Co., Ltd., Akashi-shi, Hyogo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/196,460

(22) Filed: Aug. 22, 2008

(65) Prior Publication Data

US 2008/0319338 A1 Dec. 25, 2008

Related U.S. Application Data

(60) Division of application No. 11/030,763, filed on Jan. 7, 2005, now abandoned, which is a continuation of application No. 10/018,874, filed as application No. PCT/JP01/03213 on Apr. 16, 2001, now Pat. No. 6,865,415.

(30) Foreign Application Priority Data

Apr. 18, 2000 (JP) ............................. 2000-116381

(51) Int. Cl.
 *A61B 5/05* (2006.01)
(52) U.S. Cl. ..................................... 600/547
(58) Field of Classification Search ................. 600/547
 See application file for complete search history.

(56) References Cited

U.S. PATENT DOCUMENTS 4,339,322 A 7/1982 Balko et al.
5,507,790 A * 4/1996 Weiss ......................... 128/897
5,579,782 A 12/1996 Masuo (Continued)

FOREIGN PATENT DOCUMENTS

EP 1063500 12/2000

(Continued)

OTHER PUBLICATIONS

Rankinen, T. et al. "The Prediction of Abdominal Visceral Fat Level from Body Composition and Anthropometry: ROC Analysis." International Journal of Obesity, vol. 23, pp. 801-809. Stockton Press; 1999.

(Continued)

*Primary Examiner*—Max Hindenburg
*Assistant Examiner*—Emily M Lloyd
(74) *Attorney, Agent, or Firm*—Alleman Hall McCoy Russell & Tuttle LLP

(57) ABSTRACT

A visceral fat determining device is disclosed which can be used easily at home for example and can obtain information on visceral fat. The visceral fat determining device comprises input means for inputting personal data that represents vital characteristics of the patient; a data processing unit capable of performing various calculations; and a display device capable of displaying the personal data and results of the calculations. Upon inputting of a waist size which is a girth of the trunk of the patient, and a hip size which is a girth of the buttocks of the patient, quantitative information on abdominal visceral fat of the patient is given through a calculation based on WHR which is a ratio of the waist size to the hip size (waist size/hip size).

2 Claims, 6 Drawing Sheets

U.S. PATENT DOCUMENTS 6,232,078 B1 * 5/2001 Lee et al. ........................ 435/6
6,850,797 B2 * 2/2005 Kawanishi et al. .......... 600/547
6,957,167 B2 * 10/2005 Kawanishi et al. .......... 600/547

FOREIGN PATENT DOCUMENTS

| | | |
|---|---|---|
| FR | 2731144 | 9/1996 |
| GB | 2157482 | 10/1985 |
| JP | 63140095 | 6/1988 |
| JP | 6290796 | 10/1994 |
| JP | 7079938 | 3/1995 |
| WO | 8908428 | 9/1989 |

OTHER PUBLICATIONS

International Search Report of PCT/JP2001/003213, Jun. 12, 2001, JPO.
Supplementary European Search Report of EP 01 91 9937, Mar. 8, 2004, EPO.

* cited by examiner (a)

(b)

(a)

(b)

VISCERAL FAT DETERMINING DEVICE

CROSS-REFERENCE TO RELATED APPLICATION

This application is a divisional application of U.S. patent application Ser. No. 11/030,763, filed Jan. 7, 2005, which is a continuation of U.S. patent application Ser. No. 10/018,874, filed Feb. 26, 2002, entitled VISCERAL FAT DETERMINING DEVICE, which is the U.S. National Phase of PCT International Application No. PCT/JP01/03213, filed Apr. 16, 2001, which in turn claims priority to Japanese Patent Application Serial No. 2000-116381, filed Apr. 18, 2000, all of which are incorporated by reference in their entirety for all purposes.

TECHNICAL FIELD

The present invention relates to a visceral fat determining device capable of obtaining information on visceral fat, which is part of internal body fat of a human body, through a simple operation.

BACKGROUND ART

Attention has been paid to human internal body fat in view of health maintenance. Specifically, increase in the internal body fat promotes adult diseases for example, and therefore monitoring the internal body fat can lead to prevention of these diseases and problems. There is an index called BMI for evaluating such internal body fat. Since BMI can be obtained from height and weight of a patient, it is readily used as an index for obtaining information on the internal body fat.

Another index for assessing the patient's internal body fat is body fat ratio. Recently, a variety of body fat meters capable of obtaining the body fat ratio are available on the market. By using these body fat meters, the body fat ratio as an indicator of the state of internal body fat can be obtained easily at home for example.

Incidentally, among the internal body fat, the visceral fat is believed to be a factor in particular contributing to various complications of heart diseases, diabetes, and so on. For this reason, the visceral fat is considered to be an important factor in view of health maintenance.

Here, the BMI and the body fat ratio described above are information obtained as an average data on the internal body fat as existing in the whole body. Therefore, even if BMI or the body fat ratio gives a value which does not indicate any health problems, it is not necessarily possible to determine if there is any health problem in relation with the visceral fat.

Information on the visceral fat can be obtained through a diagnosing method such as abdominal tomography by means of CT scanning, MRI and so on. Such a method allows direct observation of the abdomen itself, making it possible to obtain accurate information on the visceral fat.

However, such a diagnosis using CT scanning or the like is only possible with a large scale apparatus installed at a major hospital, and the results can be obtained only after a certain length of time necessary for measurement and data analysis. In addition, highly specific expertise is required for the operation of the apparatus and the data analysis. Therefore, the method is not available as a handy means for obtaining visceral fat information at home for example.

It is therefore an object of the present invention to provide a visceral fat determining device that can be used easily at home or the like, for obtaining information on visceral fat.

SUMMARY OF THE INVENTION

In order to achieve the object, a visceral fat determining device according to the present invention comprises input means for inputting personal data including an abdominal girth $W_L$ which is a circumferential length of a trunk of a patient and a gluteal girth $H_L$ which is a circumferential length of buttocks of the patient, a data processing unit for storing the personal data and for calculating quantitative information on abdominal visceral fat of the patient based on the personal data, and a display device for displaying the personal data and a result of the calculation performed by the data processing unit, wherein the data processing unit calculates quantitative information associated with the abdominal visceral fat of the patient based on WHR which is a ratio ($W_L/H_L$) of the abdominal girth $W_L$ to the gluteal girth $H_L$.

The state of abdominal visceral fat of the patient is believed to have a very high correlation with WHR which is one of the physical characteristics of the patient. In the visceral fat determining device according to the present invention, quantitative information on the abdominal visceral fat of the patient can be calculated based on WHR=$W_L/H_L$, namely a ratio between the gluteal girth which is a hip size of the patient and the abdominal girth $W_L$ which is a waist size of the patient. Therefore, the visceral fat determining device according to the present invention enables obtaining the information on the abdominal visceral fat which is information deeply related to the health of the patient, easily at home or the like.

According to the above visceral fat determining device, the quantitative information on the abdominal visceral fat may be an amount of the abdominal visceral fat. The amount of the abdominal visceral fat is information deeply related to the health of the patient. Therefore, by monitoring the amount of the visceral fat, it is possible to foresee a possibility of suffering from adult diseases.

The above visceral fat determining device may further comprise body fat ratio measuring means for measuring a bioelectrical impedance Z of the patient via electrodes contacted to end portions of the patient and for calculating a body fat ratio FAT of the patient based on the measured bioelectrical impedance Z and the inputted personal data or a portion thereof, and the body fat ratio FAT obtained by the body fat ratio measuring means may be displayed on the display device.

With this configuration, the visceral fat determining device according to the present invention is not only capable of obtaining information on the visceral fat but also capable of obtaining the body fat ratio FAT.

Further, the visceral fat determining device according to the present invention may be arranged so that it can calculate an estimated value of an abdominal visceral fat cross sectional area VA as information associated with the visceral fat. According to the visceral fat determining device of the present invention, when obtaining the estimated value of abdominal visceral fat cross sectional area VA, by a statistical processing to correlation between actual values of abdominal visceral fat cross sectional area VA associated with an unspecified number of human samples and their personal data including WHR, a specific correlation between the WHR and the abdominal visceral fat cross sectional area VA are determined. Then, by applying the determined correlation to each patient, the estimated value of abdominal visceral fat cross sectional area VA based on WHR and other data of each patient can be obtained at a high accuracy.

A visceral fat determining device capable of obtaining such an estimated value of abdominal visceral fat cross sectional area VA comprises: input means for inputting personal data including an abdominal girth $W_L$ which is a circumferential length of a trunk (waist size) of a patient and a gluteal girth $H_L$ which is a circumferential length of buttocks (hip size) of the patient; a data processing unit for storing the personal data and for calculating an estimated value of an abdominal visceral fat cross sectional area VA of the patient based on the personal data; and a display device for displaying the personal data and a result of the calculation performed by the data processing unit; wherein the data processing unit stores a first regression coefficient of WHR and a first regression constant, WHR being a ratio ($W_L/H_L$) of an abdominal girth $W_L$ to an gluteal girth $H_L$, the regression coefficient and the regression constant being obtained from statistical processing based on actual measurement values of the abdominal visceral fat cross sectional area VA measured in abdominal tomography of human bodies of random samples and respective WHR values of the human samples, the data processing unit calculating the estimated value of abdominal visceral fat cross sectional area VA of the patient based on a WHR value of the patient, the first regression constant of said WHR and the first regression coefficient.

The invention of to the visceral fat determining device according to the above configuration is based on the fact that the abdominal visceral fat cross sectional area VA correlates with the WHR. The data processing unit stores a first regression coefficient of the WHR and a first regression constant. The regression coefficient and the regression constant are obtained from statistical processing based on actual measurement values of the abdominal visceral fat cross sectional area VA measured in abdominal tomography of human bodies of random samples and respective WHR values of the human samples. Then, upon input of a WHR value of the patient, an estimated value of the abdominal visceral fat cross sectional area VA is calculated based on the first regression constant of the WHR and the first regression coefficient.

As described above, according to the visceral fat determining device of the present invention, the estimated value of an abdominal visceral fat cross sectional area VA can be obtained as the information associated with the visceral fat of the patient by simply inputting a WHR value which is part of the personal data. Therefore, the estimated value of abdominal visceral fat cross sectional area VA which is information deeply related to the health can be obtained easily.

Further, the visceral fat determining device capable of calculating the abdominal visceral fat cross section area VA may comprise: input means for inputting personal data including an abdominal girth $W_L$ which is a circumferential length of a trunk of a patient, a gluteal girth $H_L$ which is a circumferential length of buttocks of the patient, height and weight of the patient; a data processing unit for storing the personal data and for calculating an estimated value of an abdominal visceral fat cross sectional area VA of the patient based on the personal data; and a display device for displaying the personal data and a result of the calculation performed by the data processing unit; wherein the data processing unit stores a second regression coefficient of WHR, WHR being a ratio ($W_L/H_L$) of an abdominal girth $W_L$ to an gluteal girth $H_L$, and a first regression coefficient of BMI, BMI being an index of corpulence, and a second regression constant, the regression coefficients and the regression constant being obtained from statistical processing based on actual measurement values of the abdominal visceral fat cross sectional area VA measured in abdominal tomography of human bodies of random samples and respective WHR values and BMI values of the human samples, the data processing unit calculating the estimated value of abdominal visceral fat cross sectional area VA of the patient based on a WHR value and a BMI value of the patient, the second regression coefficient of said WHR, the first regression coefficient of said BMI and the second regression constant.

The invention which is related to this visceral fat determining device is based on the fact that the abdominal visceral fat cross sectional area VA correlates with the BMI, in addition to the WHR. The data processing unit precedently stores a second regression coefficient of the WHR, a first regression coefficient of BMI, and a second regression constant. The regression coefficients and the regression constant are obtained from statistical processing of correlation among actual measurement values of the abdominal visceral fat cross sectional area VA of human bodies of random samples and two data of WHR values and BMI values of the human samples. Then, according to this visceral fat determining device, upon input of a WHR value and a BMI value of the patient, an estimated value of the abdominal visceral fat cross sectional area VA is calculated. Therefore, according to the visceral fat determining device, in calculating the abdominal visceral fat cross sectional area VA, BMI of the patient can be reflected in addition to the WHR of the patient.

Further, the visceral fat determining device may comprise: input means for inputting personal data including an abdominal girth $W_L$ which is a circumferential length of a trunk of a patient, a gluteal girth $H_L$ which is a circumferential length of buttocks of the patient, height, weight, sex and age of the patient; a data processing unit for storing the personal data and for calculating an estimated value of an abdominal visceral fat cross sectional area VA of the patient based on the personal data; a display device for displaying the personal data and a result of the calculation performed by the data processing unit; and body fat ratio measuring means for measuring a bioelectrical impedance Z of the patient via electrodes contacted to end portions of the patient and for calculating a body fat ratio FAT of the patient based on the measured bioelectrical impedance Z and the inputted personal data or a portion thereof, wherein the data processing unit stores a third regression coefficient of WHR, WHR being a ratio ($W_L/H_L$) of an abdominal girth $W_L$ to an gluteal girth HL, a first regression coefficient of body fat ratio FAT and a third regression constant, the regression coefficients and the regression constant being obtained from statistical processing based on actual measurement values of the abdominal visceral fat cross sectional area VA measured in abdominal tomography of human bodies of random samples and respective WHR values and FAT values of the human samples, the data processing unit calculating the estimated value of abdominal visceral fat cross sectional area VA of the patient based on a WHR value of the patient, a FAT value of the patient measured by the body fat ratio measuring means, the third regression coefficient of said WHR, the first regression coefficient of said FAT and the third regression constant.

The invention of this visceral fat determining device is based on the fact that the abdominal visceral fat cross sectional area VA correlates with the body fat ratio FAT, in addition to the WHR. The data processing unit precedently stores a third regression coefficient of the WHR, a first regression coefficient of the body fat ratio FAT and a third regression constant. The regression coefficients and the regression constant are obtained from statistical processing of correlation among actual measurement values of the abdominal visceral fat cross sectional area VA of human bodies of random samples and two data of WHR values and FAT values of the human samples. According to this visceral fat determining device, upon input of a WHR value and a body fat ratio FAT of the patient, an estimated value of the abdominal visceral fat cross sectional area VA is calculated. Therefore, according to this visceral fat determining device, in calculating the abdominal visceral fat cross sectional area VA, the body fat ratio FAT of the patient can be reflected in addition to the WHR of the patient.

Further, the visceral fat determining device may comprise: input means for inputting personal data including an abdominal girth $W_L$ which is a circumferential length of a trunk of a patient, a gluteal girth $H_L$ which is a circumferential length of buttocks of the patient, height, weight and an abdominal subcutaneous fat thickness s of the patient; a data processing unit capable of storing the personal data and performing calculation of an estimated value of an abdominal visceral fat cross sectional area VA of the patient based on the personal data; and a display device for displaying the personal data and a result of the calculation performed by the data processing unit; wherein the data processing unit stores a fourth regression coefficient of WHR, WHR being a ratio ($W_L/H_L$) of an abdominal girth $W_L$ to an gluteal girth $H_L$, a second regression coefficient of BMI, BMI being an index of corpulence, a first regression coefficient of the abdominal subcutaneous fat thickness s and a fourth regression constant, the regression coefficients and the regression constant being obtained from statistical processing of correlation among actual measurement values of the abdominal visceral fat cross sectional area VA measured in abdominal tomography of human bodies of random samples and respective WHR values, BMI values and abdominal subcutaneous fat thickness values s of the human samples, the data processing unit calculating the estimated value of abdominal visceral fat cross sectional area VA of the patient based on a WHR value, a BMI value and an abdominal subcutaneous fat thickness value s of the patient, the fourth regression coefficient of said WHR, the second regression coefficient of said BMI, the first regression coefficient of said abdominal subcutaneous fat thickness value s and the second regression constant.

The invention of this visceral fat determining device is based on the fact that the abdominal visceral fat cross sectional area VA correlates with the BMI and the abdominal subcutaneous fat thickness value s, in addition to the WHR. The data processing unit stores a fourth regression coefficient of the WHR, a second regression coefficient of the BMI, a first regression coefficient of the abdominal subcutaneous fat thickness s and a fourth regression constant. The regression coefficients and the regression constant are obtained from statistical processing of correlation between actual measurement values of the abdominal visceral fat cross sectional area VA of human bodies of random samples and three kinds of data, namely, respective WHR values, BMI values and abdominal subcutaneous fat thickness values s of the human samples. According to this visceral fat determining device, upon input of a WHR value, a BMI value and an abdominal subcutaneous fat thickness value of the patient, an estimated value of the abdominal visceral fat cross sectional area VA is calculated. Therefore, according to this visceral fat determining device, in calculating the abdominal visceral fat cross sectional area VA, the BMI and the abdominal subcutaneous fat thickness s can be reflected in addition to the WHR of the patient.

Further, the visceral fat determining device according to the present invention may comprise: input means for inputting personal data including an abdominal girth $W_L$ which is a circumferential length of a trunk of a patient, a gluteal girth $H_L$ which is a circumferential length of buttocks of the patient, height, weight, sex, age and an abdominal subcutaneous fat thickness s of the patient; a data processing unit for storing the personal data and for calculating an estimated value of an abdominal visceral fat cross sectional area VA of the patient based on the personal data; a display device for displaying the personal data and a result of the calculation performed by the data processing unit; and body fat ratio measuring means for measuring a bioelectrical impedance Z of the patient via electrodes contacted to end portions of the patient and for calculating a body fat ratio FAT of the patient based on the measured bioelectrical impedance Z and the inputted personal data or a portion thereof, wherein the data processing unit stores a fifth regression coefficient of WHR, WHR being a ratio ($W_L/H_L$) of an abdominal girth $W_L$ to an gluteal girth HL, a second regression coefficient of body fat ratio FAT, a second regression coefficient of the abdominal subcutaneous fat thickness s and a fifth regression constant, the regression coefficients and the regression constant being obtained from statistical processing of correlation among actual measurement values of the abdominal visceral fat cross sectional area VA measured in abdominal tomography of human bodies of random samples, and respective WHR values, FAT values and abdominal subcutaneous fat thickness values s of the human samples, the data processing unit calculating the estimated value of abdominal visceral fat cross sectional area VA of the patient based on a WHR value of the patient, a FAT value and an abdominal subcutaneous fat thickness value s measured by the body fat measuring means, the fifth regression coefficient of said WHR, the second regression coefficient of said FAT, the second regression coefficient of said abdominal subcutaneous fat thickness s, and the fifth regression constant.

The invention of this visceral fat determining device is based on the fact that the abdominal visceral fat cross sectional area VA correlates with the body fat ratio FAT and the abdominal subcutaneous fat thickness value s in addition to the WHR. The data processing unit stores a fifth regression coefficient of the WHR, a second regression coefficient of the body fat ratio FAT, a second regression coefficient of the abdominal subcutaneous fat thickness s and a fifth regression constant. The regression coefficients and the regression constant are obtained from statistical processing of correlation between actual measurement values of the abdominal visceral fat cross sectional area VA of human bodies of random samples, and three kinds of data, namely respective WHR values, FAT values and abdominal subcutaneous fat thickness values s of the human samples. With the above constitution, according to this visceral fat determining device, upon input of a WHR value, a value of the body fat ratio FAT, a value of the abdominal subcutaneous fat thickness value s of the patient, and an estimated value of the abdominal visceral fat cross sectional area VA are calculated. Therefore, according to this visceral fat determining device, in calculating the abdominal visceral fat cross sectional area VA, the body fat ratio FAT and the abdominal subcutaneous fat thickness s can be reflected in addition to the WHR of the patient.

Further, for those visceral fat determining device to which the abdominal subcutaneous fat thickness value s is inputted, there may be such a constitution that calculation is made for an abdominal subcutaneous fat cross sectional area SA based on the abdominal subcutaneous fat thickness s and the waist size.

Further, another constitution may be such that calculation is made for a ratio between the estimated value of abdominal visceral fat cross sectional area VA and the abdominal subcutaneous fat cross sectional area SA, of the patient.

Further, another constitution may be such that calculation is made for a total abdominal fat cross sectional area WA based on the estimated value of abdominal visceral fat cross sectional area VA and the abdominal subcutaneous fat cross sectional area SA, of the patient. This visceral fat determining device capable of calculating the abdominal subcutaneous fat cross sectional area SA offers the following advantages.

Specifically, there is a recent finding about a role played by the subcutaneous fat, that the subcutaneous fat secretes a hormone that tends to reduce body fat. Further, there is another finding that that the subcutaneous fat tends to reduce adverse affects from visceral fat accumulation due to super-nutrition. Therefore, information on the abdominal subcutaneous fat and on the ratio between the abdominal subcutaneous fat and the abdominal visceral fat can be used as important index for assessing the health.

There may be another constitution other than this visceral fat determining device which is capable of calculating the abdominal visceral fat cross sectional area VA. Specifically, those which do not use the body fat ratio FAT in the calculation of the abdominal visceral fat cross sectional area VA may also be provided with the body fat ratio measuring means, so that they also obtain the body fat ratio FAT of the patient and the obtained body fat ratio FAT is displayed on the display device. This constitution allows the user to know the body fat ratio FAT in addition to the abdominal visceral fat cross sectional area VA.

Further, the visceral fat determining device according to the present invention may comprise: input means for inputting personal data including an abdominal girth $W_L$ which is a circumferential length of a trunk of a patient, and a gluteal girth $H_L$ which is a circumferential length of buttocks of the patient; a data processing unit for storing the personal data and for calculating an estimated value of an abdominal visceral fat cross sectional area VA of the patient based on the personal data; a display device for displaying the personal data and a result of the calculation performed by the data processing unit; and impedance measuring means for measuring a bioelectrical impedance Z of the patient via electrodes contacted to end portions of the patient and for calculation on the measured bioelectrical impedance Z; wherein the data processing unit stores a sixth regression coefficient of WHR, WHR being a ratio ($W_L/H_L$) of an abdominal girth $W_L$ to an gluteal girth $H_L$, a first regression coefficient of the bioelectrical impedance Z and a sixth regression constant, the regression coefficients and the regression constant being obtained from statistical processing of correlation among actual measurement values of the abdominal visceral fat cross sectional area VA measured in abdominal tomography of human bodies of random samples, and respective WHR values and bioelectrical impedance values Z of the human samples, the data processing unit calculating the estimated value of abdominal visceral fat cross sectional area VA of the patient based on a WHR value of the patient, a bioelectrical impedance value Z of the patient measured by the body fat ratio measuring means, the sixth regression coefficient of said WHR, the first regression coefficient of said bioelectrical impedance Z, and the sixth regression constant.

The invention of this visceral fat determining device is based on the fact that the abdominal visceral fat cross sectional area VA correlates with the bioelectrical impedance in addition to the WHR. The data processing unit stores a sixth regression coefficient of the WHR, a first regression coefficient of the bioelectrical impedance Z and a sixth regression constant. The regression coefficients and the regression constant are obtained from statistical processing of correlation between actual measurement values of the abdominal visceral fat cross sectional area VA of human bodies of random samples, and two kinds of data, namely respective WHR values and bioelectrical impedance values Z of the human samples. With the above constitution, according to this visceral fat determining device, upon input of a WHR value, and measurement of the bioelectrical impedance by the bioelectrical impedance measuring means, an estimated value of the abdominal visceral fat cross sectional area VA is calculated. Therefore, according to this visceral fat determining device, in calculating the abdominal visceral fat cross sectional area VA, the bioelectrical impedance can be reflected in addition to the WHR of the patient.

Further, the visceral fat determining device according to the present invention may comprise: input means for inputting personal data including an abdominal girth $W_L$ which is a circumferential length of a trunk of a patient, and a gluteal girth $H_L$ which is a circumferential length of buttocks of the patient; a data processing unit for storing the personal data and for calculating an estimated value of an abdominal visceral fat cross sectional area VA of the patient based on the personal data; a display device for displaying the personal data and a result of the calculation performed by the data processing unit; and impedance measuring means for measuring a bioelectrical impedance Z of the patient via electrodes contacted to end portions of the patient and for calculation on the measured bioelectrical impedance Z; wherein the data processing unit stores a seventh regression coefficient of WHR, and a first regression coefficient of $T_L^2/Z$ and a seventh regression constant, WHR being a ratio ($W_L/H_L$) of an abdominal girth $W_L$ to an gluteal girth $H_L$, $T_L^2/Z$ being obtained by dividing a squared height of a human by his bioelectrical impedance, the regression coefficients and the regression constant being obtained from statistical processing of correlation among actual measurement values of the abdominal visceral fat cross sectional area VA measured in abdominal tomography of human bodies of random samples, and respective WHR values and $T_L^2/Z$ values of the human samples, the data processing unit calculating the estimated value of abdominal visceral fat cross sectional area VA of the patient based on a WHR value of the patient, a bioelectrical impedance value Z of the patient measured by the body fat ratio measuring means, a height value $T_L$ inputted from the input means, the seventh regression coefficient of said WHR, the first regression coefficient of said $T_L^2/Z$, and the seventh regression constant.

The invention of this visceral fat determining device is based on the fact that the estimated value of an abdominal visceral fat cross sectional area VA correlates with $T_L^2/Z$, which is a quotient obtained by dividing a squared height $T_L$ of a human by his bioelectrical impedance. The data processing unit stores a seventh regression coefficient of the WHR, and a first regression coefficient of $T_L^2/Z$ and a seventh regression constant. The regression coefficients and the regression constant are obtained from statistical processing of correlation of actual measurement values of the abdominal visceral fat cross sectional area of human bodies of random samples with respect to two kinds of data, namely respective WHR values and $T_L^2/Z$ values of the human samples. With the above constitution, according to this visceral fat determining device, upon input of a height $T_L$ and a WHR value of the patient, and measurement of the bioelectrical impedance by the bioelectrical impedance measuring means, an estimated value of the abdominal visceral fat cross sectional area VA is calculated. Therefore, according to this visceral fat determining device, in calculating the abdominal visceral fat cross sectional area VA, the height TL and the bioelectrical impedance of the patient can be reflected in addition to the WHR of the patient.

Further, for the visceral fat determining device so far described above, another constitution may be added. Specifically, the calculation of the estimated value of abdominal visceral fat cross sectional area VA may be performed with addition of a correction term by age and a correction term by sex, of the patient. According to this constitution, in calculating the abdominal visceral fat cross sectional area VA, personal characteristics of the patient such as the age and the sex can be reflected. In this case, both of the age correction term and the sex correction term may be added, or either one of the age correction term and the sex correction term may be added.

Another possible constitution is that a plurality of ranking levels defined by a plurality of standard values are provided in advance for the abdominal visceral fat cross sectional area VA, and the estimated value of the abdominal visceral fat cross sectional area VA given by the calculation is displayed on the display device in conformity with the ranking levels. In this way, measuring results given as the quantitative information of the abdominal visceral fat cross sectional area VA can be grasped visually, in the form of ranking in graded levels. This makes easy to grasp the obtained abdominal visceral fat cross sectional area VA.

Further, for those visceral fat determining device described above, the abdominal girth $W_L$ may be provided by an abdominal girth at the fourth lumbar vertebrae of the patient, and the gluteal girth $H_L$ may be provided by a girth measured generally at the thickest portion on the buttocks of the patient. By using the waist size and hip size obtained from the above specific portions, it becomes possible to obtain measuring results which have the highest correlation with the state of visceral fat in the human body.

Further, those visceral fat determining device described above may also be provided with size measuring means for measuring the abdominal girth WL and the gluteal girth HL. The constitution allows the use of the size measuring means for on-demand, on-site measurement of the waist size and the hip size at the time when the patient wants to use the determining device, eliminating need for inputting a waist size and hip size measured elsewhere.

Another possible constitution is that the abdominal girth WL and the gluteal girth HL measured by the size measuring means are inputted to the data processing unit. This eliminates need for the patient to make an input via the input means.

PREFERRED EMBODIMENT OF THE INVENTION

An embodiment of the present invention will be described with reference to FIG. 1 through FIG. 6.

Figure 1:
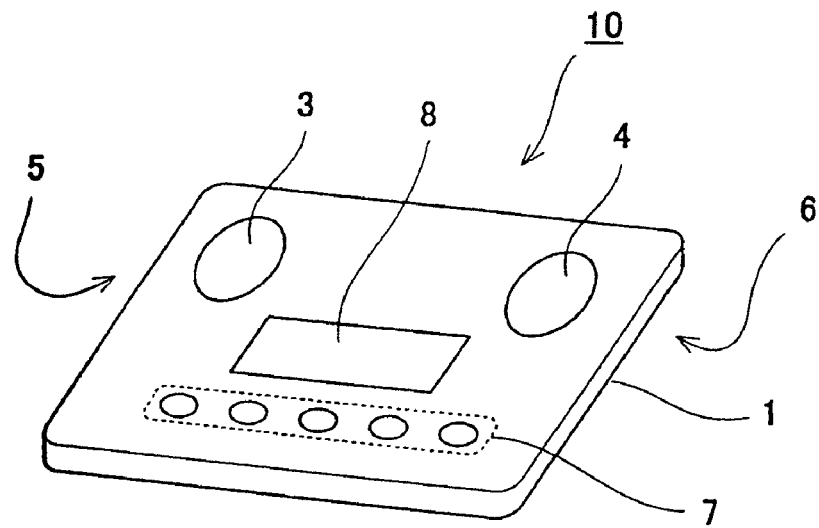
FIG. 1(a) is a perspective view of an example of a visceral fat determining device.
FIG. 1(b) shows a display example of the visceral fat determining device.
Figure 1:
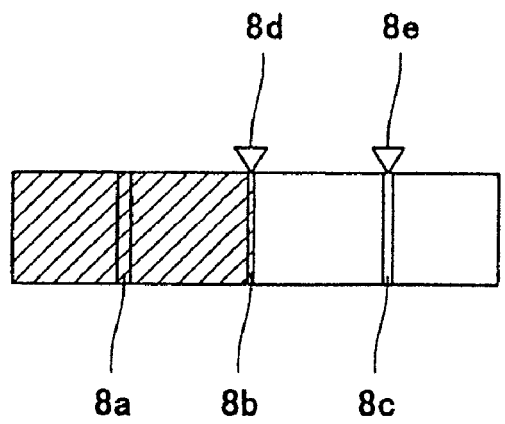

FIG. 1 shows a visceral fat determining device 10 as an embodiment of the present invention. FIG. 1(a) is a perspective view of the visceral fat determining device 10. The visceral fat determining device 10 is capable of obtaining visceral fat information of the patient such as an estimated value of abdominal visceral fat cross sectional area VA which is a cross sectional area of the visceral fat at the abdomen, and a total abdominal fat cross sectional area WA including abdominal subcutaneous fat. In addition, the determining device is provided with a built-in body fat determining device so that the body fat ratio FAT can be obtained.

Also, the visceral fat determining device 10 can obtain BMI which has been used as a handy index of corpulence. The BMI is obtained through a known formula based on the patient's height and weight as part of personal data to be described later.

The visceral fat determining device 10 is provided with an operation pad 7, which includes a plurality of keys for inputting values, characters and so on. By using these keys, the personal data which represent personal physical characteristics of the patient can be inputted, so a large number of keys necessary for the input of such personal data are provided. The input pad 7 represents the input means for inputting personal data.

The personal data which can be inputted into the visceral fat determining device 10 includes; patient's height, weight, sex, age, waist size (hereinafter may also be called "abdominal girth"), and hip size (hereinafter may also be called "gluteal girth"). The waist size ($W_L$) and the hip size ($H_L$) provide a basis for calculating WHR, which is a ratio of the waist size ($W_L$) to the hip size ($H_L$) (i.e. WHR can be obtained by dividing the waist size by the hip size.)

The waist size should preferably be a measurement of abdominal circumference measured at the fourth lumbar vertebrae of the patient. Likewise, the hip size should preferably be a circumference measured generally at the widest portion on the buttocks of the patient. It is believed that the values measured from the above specific portions can reflect the state of the body's visceral fat most accurately.

Further, the personal data to be inputted may include an abdominal subcutaneous fat thickness s. The abdominal subcutaneous fat thickness s can be measured by various known means such as so called calipers and an abdominal fat determining device based on an ultrasonic wave method.

Further, if the abdominal subcutaneous fat thickness s is measured and inputted into the visceral fat determining device, the measurement can be made at two points of the patient's body, i.e. near the navel and above the iliac bone. Then, either one of the measurements may be used as the abdominal subcutaneous fat thickness s, or a sum of the measurements may be used, or an average of the sum of the measurements may be used also.

The input pad 7 includes a variety of keys such as selection keys for selecting items of the personal data, and numeric keys for inputting values. Further, the input pad 7 includes an ON/OFF switch for turning on and off the visceral fat determining device 10, and an impedance measurement starting switch for commencing a measurement of bioelectrical impedance Z, which will be described later.

Further, by operating the input pad 7, a number of measurement modes can be selected for the measurement of the abdominal visceral fat cross sectional area VA. In accordance with the selected measurement mode, a corresponding measurement routine such as a first measurement routine and a second measurement routine is executed as will be described later.

These personal data inputted via the input pad 7, and BMI obtained from the inputted personal data are displayed on a display 8. Display of measurement results such as the body fat ratio FAT and values related to the abdominal visceral fat cross sectional area VA is also made here. FIG. 1(b) shows an example of how the display is made on the display 8.

According to the display shown in FIG. 1(b), the measured abdominal visceral fat cross sectional area VA is shown as ranked in a plurality of levels. According to FIG. 1(b), those indicated by reference numbers 8a, 8b and 8c are ranking bars showing the ranks. Specifically, for the abdominal visceral fat cross sectional area VA, a plurality of standard values are set forth in advance, and the measured value of the abdominal visceral fat cross sectional area VA is compared to these standard values to determine the rank to which the patient's abdominal visceral fat cross sectional area VA is classified. According to the example given in FIG. 1(b), the display shows the measurement which is put to a rank corresponding to the ranking bar 8b.

Further, as shown in FIG. 1(b), level indicators 8d and 8e may be displayed. The level indicators 8d and 8e may be correlated with specific symptoms related to the visceral fat. For example, clinical diagnosis sometimes concludes that the patient is corpulent if the abdominal visceral fat cross sectional area VA exceeds 100 cm². Based on this, the level indicator 8e may be set to represent 100 cm² of the abdominal visceral fat cross sectional area VA.

As shown in FIG. 1(b), the measuring results obtained as a quantitative value is displayed in ranking, or displayed with relevant information about a symptom that can be affecting the patient. These visual presentations reflecting a level of corpulence based on the measuring results allow easy understanding through a visually graded scale.

Further, the visceral fat determining device 10 is provided with a body fat ratio measuring means for measuring the body fat ratio FAT of the patient, as will be described hereinafter. Specifically, on the top surface of the visceral fat determining device 10, and closer to a forward left corner, an electrode 3 is disposed. Likewise, closer to a forward right corner, an electrode 4 is disposed. Further, on the back surface of a main body 1, and at a portion right behind the electrode 3, an electrode 5 (not shown) is disposed, and at a portion right behind the electrode 4, an electrode 6 (not shown) is disposed.

These electrodes 3, 4, 5 and 6 serve as an electrode group for measuring the bioelectrical impedance Z. The electrodes 5 and 6 serve as a pair of circuit forming electrodes for forming a path for electric current to flow within the patient's body. The electrodes 3 and 4 serve as a pair of voltage measurement electrodes for measuring electric potential difference between two points on the path.

With the above constitution, these electrodes are connected to impedance measuring means (not shown), which is well known in the art of body fat determining device, and incorporated in the main body 1. Specifically, the electrodes 5 and 6 are connected to a circuit serving as a constant current source that outputs a constant current, whereas the electrode 3 and the electrode 4 are connected to a circuit serving as a voltmeter.

When measuring the bioelectrical impedance Z via these electrodes, the patient can contact for example, his left hand thumb onto the electrode 3, and contact his left hand forefinger onto the electrode 5. Likewise, the patient can contact his right hand thumb onto the electrode 4, and contact his right hand forefinger onto the electrode 6. In this way, a bioelectrical impedance Z with the patient's hands representing the ends of the body can be measured.

As embodied in the visceral fat determining device 10, the constitution of the electrode 5 generally at right behind the electrode 3, and the electrode 6 generally at right behind the electrode 4 offers an advantage that the main body 1 can be grasped easily, with the two fingers of each hand contacted to the respective electrodes. The constitution enables holding the visceral fat determining device 10 stably in the hands and measurement of the bioelectrical impedance Z under a stable condition. Further, the constitution allows the electrodes 3 and 5 to be pressed generally evenly by the two respective fingers, as well as allowing the electrodes 4 and 6 to be pressed generally evenly by the respective two fingers, enabling measurement of the bioelectrical impedance Z more stably.

Figure 2:
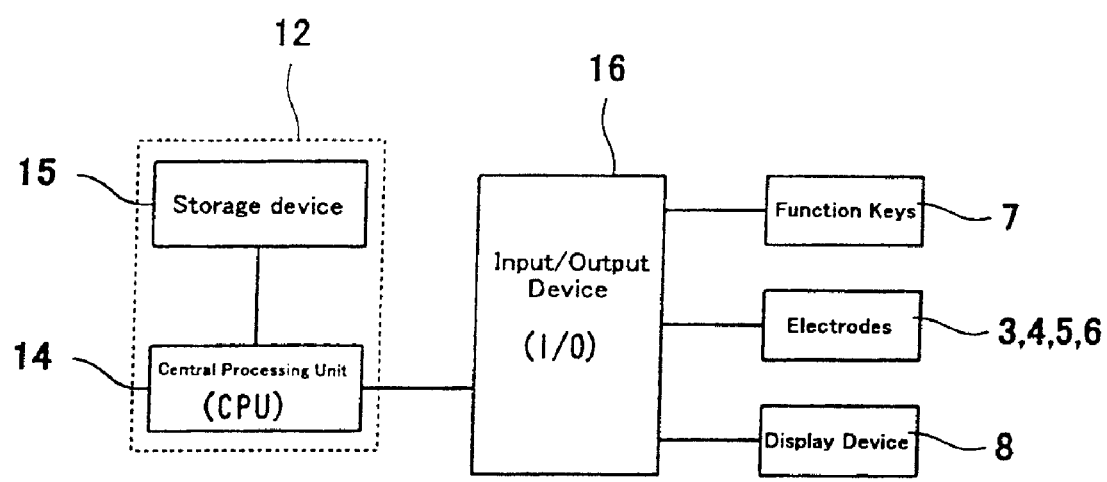
FIG. 2 is a block diagram associated with a signal processing in the visceral fat determining device.

Next, reference is made to FIG. 2 to describe signal processing blocks in the visceral fat determining device 10. Various calculations made within the visceral fat determining device 10 are performed by a calculation device 12 which includes a central processing unit (CPU) 14 and the storage device 15.

The storage device 15 stores personal data inputted through the function keys provided in the operation pad 7, and measured values of the bioelectrical impedance Z obtained through the electrodes 3, 4, 5 and 6. The storage device 15 also stores various formulae, coefficients and so on necessary for obtaining the body fat ratio FAT based on the bioelectrical impedance Z and the personal data. Also, when the body fat ratio FAT is thus calculated, the obtained body fat ratio FAT is stored in the storage device 15. Still further, when a BMI value and an estimated value of the abdominal visceral fat cross sectional area VA are obtained, these calculation results are also stored in the storage device 15.

Further, the storage device 15 stores an operation instruction routine which includes procedures for providing the patient with necessary guidance and instructions on how to operate the visceral fat determining device 10, measuring routines which include calculation steps for obtaining the BMI, the body fat ratio FAT, and the estimated value of the abdominal visceral fat cross sectional area VA. The measuring routine includes the first measuring routine and the second measuring routine to be detailed later in a description of an operation example.

Still further, the storage device 15 stores the following coefficients to be used for obtaining the estimated abdominal visceral fat cross sectional area VA: a first regression coefficient $a_1$ of WHR, a second regression coefficient $a_2$ of WHR, a third regression coefficient $a_3$ of WHR, a fourth regression coefficient $a_4$ of WHR, a fifth regression coefficient $a_5$ of WHR, a sixth regression coefficient $a_6$ of WHR, a seventh regression coefficient $a_7$ of WHR, a first regression coefficient $b_1$ of BMI, a second regression coefficient $b_2$ of BMI, a first regression coefficient $d_1$ of the body fat ratio FAT, a second regression coefficient $d_2$ of the body fat ratio FAT, a first regression coefficient $e_1$ of the abdominal subcutaneous fat thickness s, a second regression coefficient $e_2$ of the abdominal subcutaneous fat thickness s, a first regression coefficient $f_1$ of the bioelectrical impedance, and a first regression coefficient $g_1$ of $T_L^2/Z$, a first regression constant $c_1$, a second regression constant $c_2$, a third regression constant $c_3$, a fourth regression constant $c_4$, a fifth regression constant $c_5$, a sixth regression constant $c_6$, and a seventh regression constant $c_7$.

These coefficients and constants a1, a2, a3, a4, a5, a6, a7, b1, b2, c1, c2, c3, c4, c5, c6 c7, d1, d2, e1, e2, f1, and g1 are obtained elsewhere, and then inputted to the visceral fat determining device 10 for storage. These coefficients are obtained in the following procedure. Specifically, for a mass of unspecified individuals, measurements are made for their individual actual abdominal visceral fat cross sectional area VA. Measurements are also made for the WHR, BMI, the body fat ratio FAT, and the abdominal subcutaneous fat thickness s for each of the individuals.

Correlation between WHR and the actual abdominal visceral fat cross sectional area VA is statistically processed, whereby $a_1$ and the first regression constant $c_1$ with respect to the WHR can be obtained. Also, correlation among WHR, BMI and the actual abdominal visceral fat cross sectional area VA is statistically processed, whereby $a_2$ with respect to the WHR, and $b_1$ and the second regression constant $c_2$ with respect to the BMI can be obtained. Further, correlation among WHR, the body fat ratio FAT and the actual abdominal visceral fat cross sectional area VA is statistically processed, whereby $a_3$ with respect to the WHR, and $d_1$ and the third regression constant $c_3$ with respect to the body fat ratio FAT can be obtained.

Further, correlation among WHR, BMI, the abdominal subcutaneous fat thickness and the actual abdominal visceral fat cross sectional area VA is statistically processed, whereby $a_4$ with respect to WHR, $b_2$ with respect to BMI, $e_1$ with respect to the abdominal subcutaneous fat thickness s and the fourth regression constant $c_4$ can be obtained. Further, correlation of WHR, BMI, the abdominal subcutaneous fat thickness s, and the actual abdominal visceral fat cross sectional area VA is statistically processed, whereby $a_5$ with respect to the WHR, $d_2$ with respect to the body fat ratio FAT, $e_2$ with respect to the abdominal subcutaneous fat thickness s and the fifth regression constant $c_5$ can be obtained.

Further, correlation among WHR, the bioelectrical impedance Z and the actual abdominal visceral fat cross sectional area VA is statistically processed, whereby $a_6$ with respect to WHR, $f_1$ with respect to the bioelectrical impedance Z and the sixth regression constant $c_6$ can be obtained. Further, correlation of WHR, $T_L^2/Z$ and the actual abdominal visceral fat cross sectional area VA is statistically processed, whereby $a_7$ with respect to WHR, $g_1$ with respect to $T_L^2/Z$, and the seventh regression constant $c_7$ can be obtained.

In order to obtain these coefficients $a_1$ through $g_1$, regression analysis can be employed for the statistical processing of the correlation between the actual abdominal visceral fat cross sectional area VA and individual personal data. For example, the coefficient $a_1$ with respect to WHR, and the constant $c_1$ which can be obtained from the correlation with $a_1$ can be obtained by single regression analysis based on a hypothesis that the actual abdominal visceral fat cross sectional area VA is correlated only with WHR. On the other hand, if the abdominal visceral fat cross sectional area VA is assumed to correlate with WHR and other personal data, each coefficient can be obtained by multiple regression analysis.

In order to obtain the actual abdominal visceral fat cross sectional area VA of the unspecified people who provide sample data, tomography is employed. The tomography can be provided by CT scanning, MRI, ultrasonic diagnosis or any other methods capable of performing accurate measurement of a human abdominal cross section. In obtaining the coefficients $a_1$ through $e_2$, actual number of people who provide sample data on the abdominal visceral fat cross sectional area VA and the personal data should desirably be not smaller than 100, in consideration that statistical processing must be made to the abdominal visceral fat cross sectional area VA. More desirably, the number of people should be not smaller than 500.

In the signal processing blocks of the visceral fat determining device 10 shown in FIG. 2, the data stored in the storage device and measurement values described above can be displayed on the display 8. Input and output of these data and measurements to and from the central processing unit 14 and the storage device 15 are performed via an input/output device (I/O) 16.

Next, an example operation of the visceral fat determining device 10 will be described with reference to FIG. 3. First, the power of the visceral fat determining device 10 is turned on. When selection is made on the operation pad 7 for the first measurement mode, then the first measuring routine is started.

In the beginning, the personal data is inputted which is body specific information. Namely, the height, weight, age, sex and WHR are inputted as body specific information including and stored (S1).

Next, a calculation is made to obtain and store BMI based on the height and the weight inputted in step S1 (S2). Then, bioelectrical impedance Z between the patient's hands is measured (S3), and the measured bioelectrical impedance Z is stored. Using the bioelectrical impedance Z and other necessary personal data, body fat ratio FAT is calculated and stored (S4).

Next, abdominal visceral fat cross sectional area VA is estimated by calculation (S5) based on WHR. Then, the obtained BMI, the body fat ratio FAT and the abdominal visceral fat cross sectional area VA are displayed on the display 8 (S6).

[The calculation for estimating the abdominal visceral fat cross sectional area VA in step S5 is performed by using the following formula (1):

$$VA = a_1 \cdot WHR + c_1 \quad (1)$$

In the formula (1), VA represents the abdominal visceral fat cross sectional area (Hereinafter, VA represents the abdominal visceral fat cross sectional area.).

Figure 3:
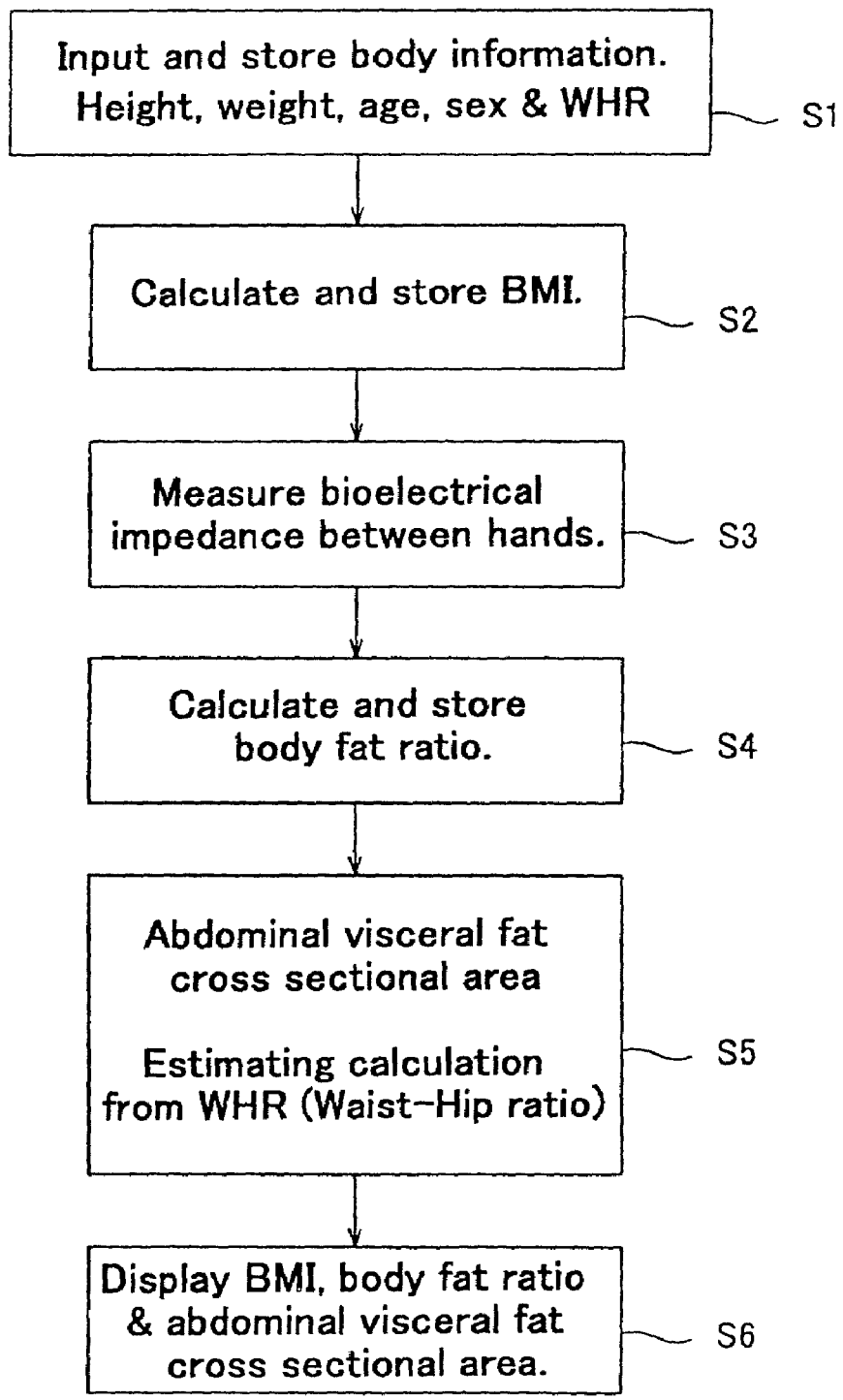
FIG. 3 is a flowchart showing an example of procedure in a measurement of abdominal visceral fat cross sectional area VA.

In step S5 shown in FIG. 3, VA is assumed to correlate only with the patient's WHR, the coefficient $a_1$ and the constant $c_1$ are derived on this assumption, and VA is calculated with this coefficient, constant, and WHR. In calculating the estimated VA, alternatively to the formula (1), one of the following formulae (2) through (7) may be utilized:

$$VA = a_2 \cdot WHR + b_1 \cdot BMI + c_2 \quad (2)$$

$$VA = a_3 \cdot WHR + d_1 \cdot FAT + c_3 \quad (3)$$

$$VA = a_4 \cdot WHR + b_2 \cdot BMI + e_1 \cdot s + c_4 \quad (4)$$

$$VA = a_5 \cdot WHR + d_2 \cdot FAT + e_2 \cdot s + c_5 \quad (5)$$

$$VA = a_6 \cdot WHR + f_1 \cdot Z + c_6 \quad (6)$$

$$VA = a_7 \cdot WHR + g_1 \cdot T_L^2/Z + c_7 \quad (7)$$

FAT used in the formulae (3) and (5) is the body fat ratio expressed in percentage. (Hereinafter, FAT represents the body fat ratio.) Also, the character s in the formula (4) represents the abdominal subcutaneous fat thickness. Formula (2) is for a calculation of an estimated VA based on correlation of VA with the patient's WHR and BMI. Formula (3) is for a calculation of an estimated VA based on correlation of VA with the patient's WHR and FAT.

Further, Formula (4) is for a calculation of an estimated VA based on correlation of VA with the patient's WHR, BMI and abdominal subcutaneous fat thickness s. Likewise, Formula (5) is for a calculation of an estimated VA based on correlation of VA with the patient's WHR, FAT and the abdominal subcutaneous fat thickness s.

Further, Formula (6) is for a calculation of an estimated VA based on correlation of VA with the patient's WHR and bioelectrical impedance Z. Still further, Formula (7) is for a calculation of an estimated VA based on correlation of VA with the patient's WHR and $TL^2/Z$.

As will be understood from the above, Formula (1) gives VA based only on correlation of VA with the patient's WHR. On the other hand, Formulae (2) through (7) give VA based on correlation with a plurality of values from the personal data. Such a method as in Formulae (2) through (7), of calculating the estimated VA based on correlation with a plurality of values from the personal data enables to obtain VA with more precise reflection of the patient's personal physical characteristics.

In addition, each of the Formulae (1) through (7) may include correction terms on the basis of age and sex. The age correction term Yc is given by Formula (8), whereas the sex correction term Xc is given by Formula (9):

$$Yc = -\delta \cdot age \tag{8}$$

$$Xc = \eta \cdot sex \tag{9}$$

In Formula (8), "age" represents the age of the patient, and $\delta$ represents an age correction coefficient. In Formula (9), "sex" is a variable which depends upon whether the patient is male or female, and $\eta$ represents a sex correction coefficient. If these correction terms are added to Formulae (1) through (7), these terms are defined and treated as variable terms of the multiple regression equation. Therefore, $\delta$ in Formula (8) can be obtained as a regression variable, "age" can be obtained as a variable, $\eta$ in Formula (9) can be obtained as a regression coefficient, and "sex" can be obtained as a variable, each based on correlation with the estimation formula for VA.

If these Formulae (1) through (7) are used with the addition of the correction term Yc given by Formula (8) and the correction term Xc give by Formula (9) in the calculation of VA, it becomes possible to reflect the patient's personal physical characteristics in terms of the age and sex more precisely. Either one or both of the correction terms Yc and Xc may be added to any of the formulae (1) through (7). If both of the Yc and Xc are added in the calculation using anyone of the formulae (1)-(7), it becomes possible to obtain the VA with more precise reflection of the patient's personal physical characteristics.

Further, based on the abdominal visceral fat cross sectional area VA thus obtained, an amount of the abdominal visceral fat can be calculated as additional information on the visceral fat.

Figure 4:
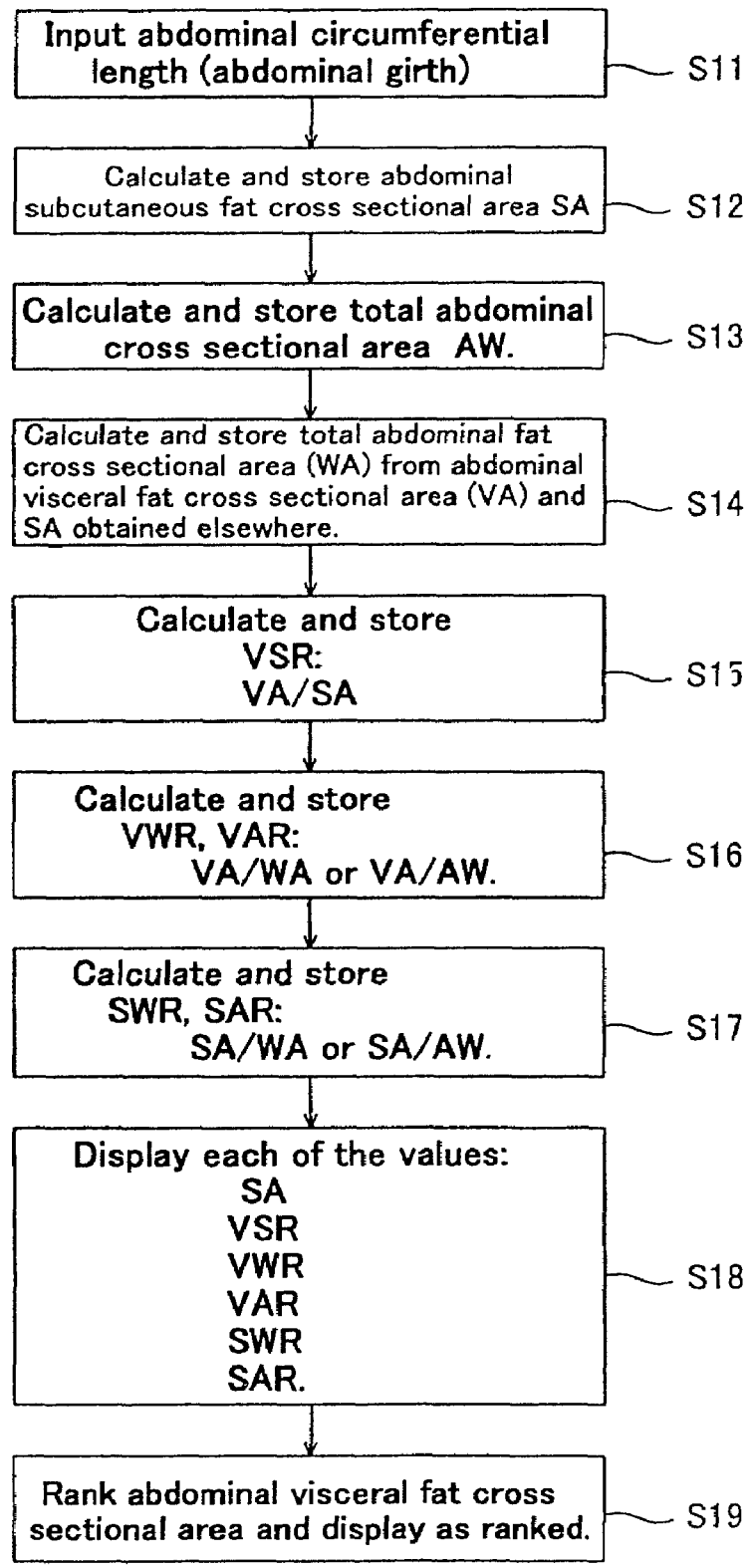
FIG. 4 is a flowchart showing the example procedure of a measurement of abdominal visceral fat cross sectional area VA.

Next, another example operation of the visceral fat determining device 10 will be described with reference to FIG. 4. When selection is made on the operation pad 7 (FIG. 1) for the second measurement mode, then the second measuring routine is started. Firstly, the patient is prompted to input his waist size or the abdominal girth (S11). Next, a calculation is made for an abdominal subcutaneous fat cross sectional area SA, and the obtained value is stored (S12). The calculation performed in step S12 uses the following Formula (10):

$$SA = W_L \cdot s - \pi \cdot s^2 \tag{10}$$

In formula (10), $W_L$ represents the abdominal girth, and character "s" represents the abdominal subcutaneous fat thickness.

Next, a total abdominal cross sectional area (AW) is calculated and stored (S13). The calculation performed in step S13 uses the following Formula (11):

$$AW = \zeta \cdot (W_L^2 / 4\pi) \tag{11}$$

In formula (11), character $\pi$ represents the circular constant pi. Further, character $\zeta$ represents a conversion coefficient for a conversion between circular and oval circumferences.

Next, based on the abdominal visceral fat cross sectional area VA and SA obtained and stored separately, the total abdominal fat cross sectional area WA is calculated and stored (S14). The calculation performed in step S14 uses the following Formula (12):

$$WA = VA + SA \tag{12}$$

Next, a VSR which is a ratio between the abdominal visceral fat cross sectional area VA and abdominal subcutaneous fat cross sectional area SA is calculated and stored (S15). The calculation performed in step S15 uses the following Formula (13):

$$VSR = VA/SA \tag{13}$$

Next, a VWR which is a ratio between the abdominal visceral fat cross sectional area VA and the total abdominal cross sectional area WA, and a VAR which is a ratio between the abdominal visceral fat cross sectional area VA and the total abdominal cross sectional area (AW) are calculated and stored (S16). The calculations performed in step S16 use Formula (14) for obtaining VWR and Formula (15) for obtaining VAR:

$$VWR = VA/WA \tag{14}$$

$$VAR = VA/AW \tag{15}$$

Next, calculations are made for SWR which is a ratio between the abdominal subcutaneous fat cross sectional area SA and the total abdominal cross sectional area WA, and SAR which is a ratio between the abdominal subcutaneous fat cross sectional area SA and the total abdominal cross sectional area (AW), and the calculated values are stored (S17). The calculations performed in step S17 use Formula (16) for obtaining SWR and Formula (17) for obtaining SAR:

$$SWR = SA/WA \tag{16}$$

$$SAR = SA/AW \tag{17}$$

Next, obtained values of SA, VSR, VWR, VAR, SWR and SAR are displayed on the display 8 (S18). Further, the abdominal subcutaneous fat cross sectional area SA is ranked in a plurality of levels and displayed on the display 8 in conformity to the ranking (S19).

In the above description based on FIG. 1 through FIG. 4, the personal data such as the waist size, the hip size and ratio WHR thereof are measured elsewhere and then manually inputted using the operation pad 7. Alternatively, however, the visceral fat determining device may incorporate size measuring means capable of measuring the patient's abdominal girth. FIG. 5(a) gives an example of such a visceral fat determining device, showing a visceral fat determining device 20 incorporating the size measuring means, in a fragmentally transparent perspective view.

The visceral fat determining device 20 is provided with a measuring tape 21 serving as the size measuring means, which can be drawn in and pulled out of the main body. The measuring tape 21 has its end provided with a pull tip 22, which can be grabbed and pulled to draw the tape out of a pull portion 23. Further, the measuring tape 21 can be reeled back into the main body when a rewind button (not shown) provided in the visceral fat determining device 20 is operated.

Further, on the side away from the side, on which pull portion 23 is formed, of the visceral fat determining device 20, an engaging portion 24 is provided. As shown in FIG. 5(b), the pull tip 22 of the measuring tape 21 can be hooked onto the engaging portion 24, which prevents the measuring tape 21 from slackening, and enables it to measure accurately.

With the above constitution, as shown in FIG. 5(b), when measuring the size of a required portion, the measuring tape 21 can be pulled out and wound around the abdomen, the hips and so on, and then the pull tip 22 is hooked on the engaging portion 24 to read the tape.

The waist size and the hip size measured with the measuring tape 21 may be manually inputted via the operation pad 7. Alternatively however, the size measured with the measuring tape 21 may be directly inputted to calculating device 12 without the operation on the operation pad 7. In this case, size data obtained through the measurement by the measuring tape 21 should be processed as a digital signal, and is inputted to the data processing unit 12 by the signal processing block shown in FIG. 2 via the input/output device (I/O) 16. Then, based on the waist size and the hip size measured by the measuring tape 21, their ratio or WHR is obtained by the data processing unit 12.

As exemplified by the visceral fat determining device 20, if the size measuring means is provided so that the hip size and the waist size can be measured on demand, the measurement can be performed right at the time when the visceral fat cross sectional area is to be obtained. Therefore, the abdominal visceral fat cross sectional area VA can be obtained more accurately from the latest hip size and the waist size.

Alternatively to the measuring tape 21, the size measuring means may be provided by an unillustrated roller that serves as a rolling distance determining device. Specifically, the size measuring means can be provided by a roller, which is rolled on and along a portion to be measured, and the travel distance of the roller obtained from the number of roller rotations is translated to the size. If the size measuring means is provided by such a rolling type measurer, measuring of the waist or hips can be made very easily by simply rolling the roller around the waist or the hips.

The embodiments given as the visceral fat determining device 10 and the visceral fat determining device 20 are handheld apparatuses, and the bioelectrical impedance Z in relation to the body fat ratio FAT is measured via the hands.

Figure 6:
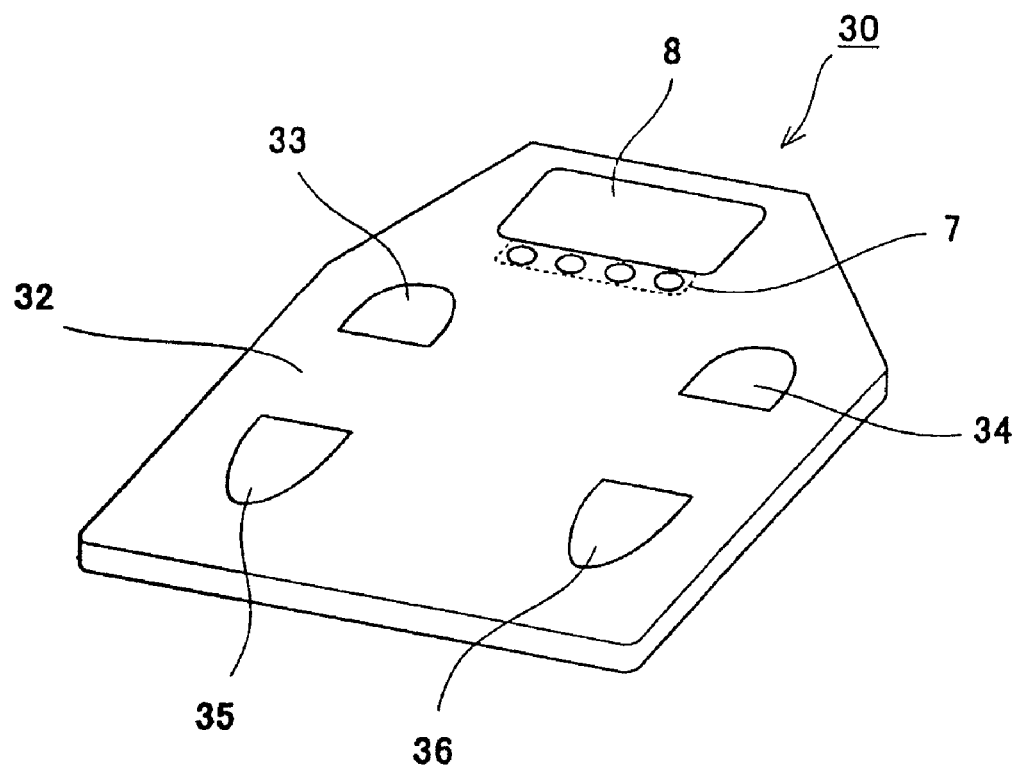
FIG. 6 is a perspective view of a visceral fat determining device.

The visceral fat determining device according to the present invention can also be embodied as incorporated in a weight scale or body fat determining device. Specifically, a visceral fat determining device 30 shown in FIG. 6 is incorporated integrally with a weight scale.

According to the visceral fat determining device 30, a main body has a top surface formed with a weight measuring surface 32, and the weight on the weight measuring surface 32 is detected by a load cell (not shown) provided inside the main body. The patient stands on the weight measuring surface 32 to obtain the weight.

Further, the weight measuring surface 32 is provided with the electrodes 33, 34, 35 and 36 for measuring the patient's bioelectrical impedance Z. The electrodes 33 and 34 serve as a pair of circuit forming electrodes for forming a path for electric current to flow within the patient's body. The electrodes 35 and 36 serve as a pair of voltage measurement electrodes for measuring electric potential difference between two points on the circuit.

These electrodes 33, 34, 35 and 36 are, as in the visceral fat determining device 10 and the visceral fat determining device 20, connected to impedance measuring means which is well known in the art of body fat determining device, so that the body's impedance can be measured via the electrodes 33, 34, 35 and 36.

According to the visceral fat determining device 30, when measuring the bioelectrical impedance Z, the patient stands on the measuring surface 32, with the sole of his left foot onto electrodes 33 and 35, and the sole of his right foot onto electrodes 34 and 36. Through this, the patient's weight is measured as well as his bioelectrical impedance Z, with his feet representing the ends of the body.

The visceral fat determining device 30 is provided with the same operation pad 7 and the display 8 as described for the visceral fat determining device 10, as well as the data processing unit 12 that includes the central processing unit 14 and the storage device 15.

The storage device 15 is constructed, just as described for the visceral fat determining device 10, stores the routines, the coefficients and data, as well as inputted data and measurement results. Further, signal processing is also performed in the same way as described with reference to FIG. 2.

A note should be made however, that according to the visceral fat determining device 30, the patient's weight detected by the load cell which is provided inside the main body is automatically processed as weight data, by the data processing unit 12. Further, the patient's weight as one of the personal data may not be manually inputted from the operation pad 7, but instead the weight data measured by the visceral fat determining device 30 can be used.

Still further, the visceral fat determining device 30 may be provided with the size measuring means which has been described for the visceral fat determining device 20, so that the waist size and hip size can be readily measured.

In the visceral fat determining device 30 described above, a weight scale is integrally incorporated so that the patient's weight can be measured while he is standing on the determining device to measure the bioelectrical impedance Z via his feet and thereby measuring the body fat ratio FAT. Alternatively however, components providing the weight scale may not be included. Specifically, the determining device may not be able to measure the weight, but can measure the bioelectrical impedance Z via the feet, and can measure the body fat ratio FAT based on the impedance Z, as well as the above-described measurements associated with the visceral fat.

Figure 5:
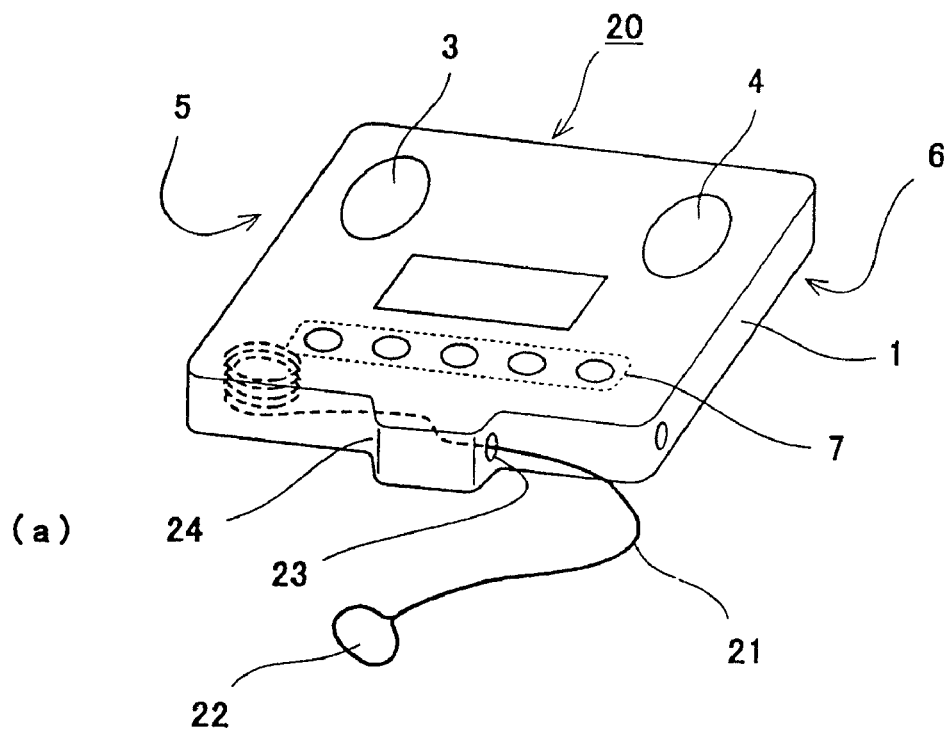
FIGS. 5(a) and 5(b) are illustrations showing a visceral fat determining device provided with a dimension measuring means.
Figure 5:
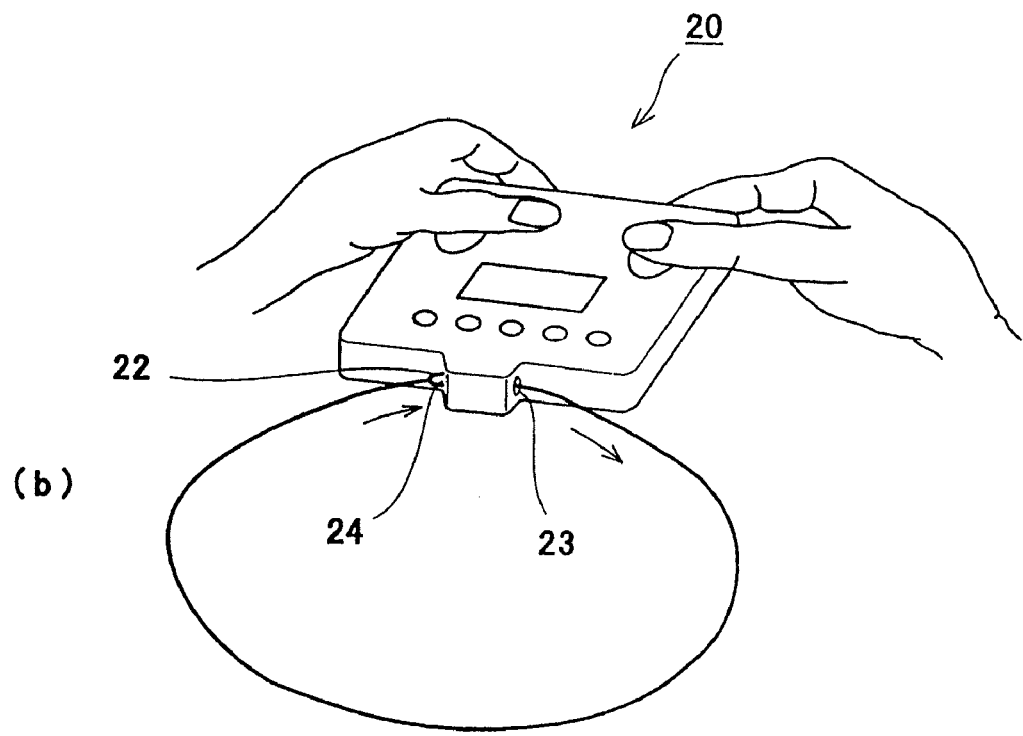

Further, additional constitution may be made for the body fat ratio measuring means so that impedance measurement can be performed via both the hand and the feet as well as the above-described measurements associated with the visceral fat can be performed. Specifically, the body fat ratio measuring means is arranged as shown in FIG. 1 and FIG. 5 so that the impedance measurement can be performed, in addition to the capability of the impedance measurement via the feet as shown in FIG. 6.

As has been described, according to the visceral fat determining device of the present invention, the patient's abdominal visceral fat cross sectional area VA can be obtained easily at home for example. This offers an advantage that information on the visceral fat which is believed to be important with respect to various diseases can be obtained easily.

What is claimed is:

1. A visceral fat determining device comprising:
    input means for inputting personal data including an abdominal girth $W_L$ which is a circumferential length of a trunk of a patient, a height value $T_L$ of the patient, and a gluteal girth $H_L$ which is a circumferential length of buttocks of the patient;
    a data processing unit for storing the personal data and for calculating an estimated value of an abdominal visceral fat cross sectional area VA of the patient;
    a display device for displaying the personal data and the result of the abdominal visceral fat cross sectional area VA calculation performed by the data processing unit; and
    impedance measuring means for measuring a bioelectrical impedance value Z of the patient via electrodes contacted to end portions of the patient;

wherein the data processing unit is programmed for storing a first regression coefficient of WHR, and a second regression coefficient of $T_L^2/Z$ and a first regression constant, WHR being a ratio ($W_L/H_L$) of an abdominal girth $W_L$ to a gluteal girth $H_L$, $T_L^2/Z$ being obtained by dividing a squared height of a human $T_L^2$ by the human's bioelectrical impedance value Z, the regression coefficients and the regression constant being obtained from statistical processing of correlation among actual measurement values of the abdominal visceral fat cross sectional area VA measured via abdominal tomography of random samples of human bodies, and respective WHR values and $T_L^2/Z$ values of the human samples;

wherein the data processing unit is further programmed for calculating the estimated value of abdominal visceral fat cross sectional area VA of the patient based on the sum of the first regression coefficient multiplied by the WHR value of the patient, the second regression coefficient multiplied by the $T_L^2/Z$ value of the patient, and the first regression constant.

2. A visceral fat determining method comprising:

at a data processing unit, receiving from an input means input of personal data including an abdominal girth $W_L$ which is a circumferential length of a trunk of a patient, a height value $T_L$ of the patient, and a gluteal girth $H_L$ which is a circumferential length of buttocks of the patient;

storing the personal data at the data processing unit;

measuring, via an impedance measuring means, a bioelectrical impedance value Z of the patient via electrodes contacted to end portions of the patient;

at the data processing unit, storing a first regression coefficient of WHR, and a second regression coefficient of $T_L^2/Z$ and a first regression constant, WHR being a ratio ($W_L/H_L$) of an abdominal girth $W_L$ to a gluteal girth $H_L$, $T_L^2/Z$ being obtained by dividing a squared height of a human $T_L^2$ by the human's bioelectrical impedance value Z, the regression coefficients and the regression constant being obtained from statistical processing of correlation among actual measurement values of an abdominal visceral fat cross sectional area VA measured via abdominal tomography of random samples of human bodies, and respective WHR values and $T_L^2/Z$ values of the human samples;

at the data processing unit, calculating an estimated value of the abdominal visceral fat cross sectional area VA of the patient based on the sum of the first regression coefficient multiplied by the WHR value of the patient, the second regression coefficient multiplied by the $T_L^2/Z$ value of the patient, and the first regression constant; and displaying the personal data and the result of the abdominal visceral fat cross sectional area VA calculation on a display.

* * * * *